US011204241B2

(12) United States Patent
Bilodeau et al.

(10) Patent No.: US 11,204,241 B2
(45) Date of Patent: Dec. 21, 2021

(54) METHODS FOR MEASURING PROPERTIES OF ROCK PIECES

(71) Applicants: Her Majesty The Queen in Right of Canada as Represented by the Minister of Natural Resources Canada, Ottawa (CA); Institut National d'Optique/National Optics Institute, Quebec (CA)

(72) Inventors: Magella Bilodeau, Gatineau (CA); Andre Demers, Ottawa (CA); Daniel Lefebvre, Quebec (CA); Sebastien Roy, Quebec (CA)

(73) Assignees: Her Majesty The Queen in Right of Canada as Represented by the Minister of Natural Resources Canada, Ottawa (CA); Institut National d'Optique/National Optics Institute, Québec (CA)

(*) Notice: Subject to any disclaimer, the term of this patent is extended or adjusted under 35 U.S.C. 154(b) by 276 days.

(21) Appl. No.: 16/486,065

(22) PCT Filed: Feb. 15, 2018

(86) PCT No.: PCT/CA2018/050171
§ 371 (c)(1),
(2) Date: Aug. 14, 2019

(87) PCT Pub. No.: WO2018/148832
PCT Pub. Date: Aug. 23, 2018

(65) Prior Publication Data
US 2020/0041264 A1 Feb. 6, 2020

(30) Foreign Application Priority Data
Feb. 16, 2017 (GB) .................................. 1702530

(51) Int. Cl.
G06K 9/00 (2006.01)
G01B 11/25 (2006.01)
(Continued)

(52) U.S. Cl.
CPC ........... *G01B 11/2545* (2013.01); *G01N 3/40* (2013.01); *G01N 15/0227* (2013.01);
(Continued)

(58) Field of Classification Search
CPC . G01B 11/00; G01B 11/2518; G01B 11/2545; G01N 15/0227; G01N 15/1463;
(Continued)

(56) References Cited

U.S. PATENT DOCUMENTS 4,105,925 A * 8/1978 Rossol ................. G01B 11/002
250/559.36
4,497,576 A * 2/1985 Caussignac ........ G01N 15/0227
250/222.2
(Continued)

FOREIGN PATENT DOCUMENTS

EP 1 464 949 A2 10/2004

OTHER PUBLICATIONS

Bilodeau et al. (2008) "Impact of electronic blasting detonators on downstream operations of a quarry," Minerals & Metallurgical Processing 25(1):32-40.
(Continued)

*Primary Examiner* — Avinash Yentrapati
(74) *Attorney, Agent, or Firm* — Leydig, Volt & Mayer, Ltd.

(57) ABSTRACT

Provided herein is a method for measuring the size distribution and/or hardness of free falling rock pieces. The method comprises projecting at least one laser line on the falling rock pieces by a laser device; capturing images of the falling rock pieces at an angle from the at least one laser line
(Continued)

by at least one camera; and obtaining size distribution data of the falling rock pieces based on data obtained from a topographical map generated from the captured images. Certain embodiments further comprise: obtaining at least one of the volume and area of individual rock pieces from the topographical map; conducting a data analysis on at least one of the volume and area measurements of the rock pieces to reduce at least one of sampling and measurement errors; determining the size distribution of the falling rock pieces based on the data analysis and, optionally, evaluating a rock hardness index for the rock. Further provided is a method comprising: producing two topographical maps of the pieces from captured images; and obtaining the volume of pieces from the topographical map by adding half-volumes from each of the topographical maps.

29 Claims, 12 Drawing Sheets

(51) Int. Cl.
*G06T 7/62* (2017.01)
*G01N 3/40* (2006.01)
*G01N 15/02* (2006.01)
*G01N 21/85* (2006.01)
*G01N 33/24* (2006.01)
*G01N 15/14* (2006.01)

(52) U.S. Cl.
CPC .............. *G01N 21/85* (2013.01); *G01N 33/24* (2013.01); *G06T 7/62* (2017.01); *G01N 2015/1493* (2013.01); *G01N 2015/1497* (2013.01); *G06T 2207/10021* (2013.01); *G06T 2207/30181* (2013.01)

(58) Field of Classification Search
CPC ... G01N 2015/1493; G01N 2015/1497; G01N 2021/8592; G01N 21/85; G01N 33/24; G06T 7/521; G06T 7/62
See application file for complete search history.

(56) References Cited

U.S. PATENT DOCUMENTS

| | | | | |
|---|---|---|---|---|
| 5,011,285 | A | * | 4/1991 | Jorgensen .......... G01N 15/0227 356/335 |
| 5,426,501 | A | * | 6/1995 | Hokanson .......... G01N 15/1456 250/222.2 |
| 5,519,793 | A | * | 5/1996 | Grannes .................... G06T 7/44 382/199 |
| 7,020,307 | B2 | | 3/2006 | Hinton et al. |
| 8,233,667 | B2 | | 7/2012 | Helgason et al. |
| 2002/0170367 | A1 | * | 11/2002 | Lieber .................... G05B 15/02 73/866.5 |
| 2003/0029946 | A1 | * | 2/2003 | Lieber .................... B02C 25/00 241/34 |
| 2003/0156739 | A1 | | 8/2003 | Hinton et al. |
| 2018/0120214 | A1 | * | 5/2018 | Kato ...................... G01N 15/10 |
| 2020/0041264 | A1 | * | 2/2020 | Bilodeau ................ G01B 11/00 |
| 2020/0064169 | A1 | * | 2/2020 | Kato ........................ G01F 1/712 |
| 2020/0249058 | A1 | * | 8/2020 | Malos ...................... G01F 1/74 |

OTHER PUBLICATIONS

Couët et al. (Jul. 2018) "Applying online ore hardness estimation to SAG operation and optimisation," IMPC 2016: XXVIII International Mineral Processing Congress Proceedings, pp. 1-10, Curran Associates, Inc., New York, meeting held Sep. 11-15, 2016.
International Preliminary Report on Patentability, dated Aug. 20, 2019, corresponding to International Application No. PCT/CA2018/050171 (filed Feb. 15, 2018), 6 pp.
Search Report and Written Opinion, dated May 22, 2018, corresponding to International Application No. PCT/CA2018/050171 (filed Feb. 15, 2018), 10 pp.
"W.S. Tyler CPA," Available online at https://wstyler.com/particle-analysis/wstyler-cpa/, Accessed Feb. 13, 2020, 28 pp.

* cited by examiner

METHODS FOR MEASURING PROPERTIES OF ROCK PIECES

CROSS-REFERENCE TO RELATED APPLICATION(S)

This application is a U.S. National Stage Application filed under 35 U.S.C. § 371 of International Application No. PCT/CA2018/050171, filed Feb. 15, 2018, which claims the benefit of United Kingdom Patent Application No. 1702530.5, filed Feb. 16, 2017. Each of these applications is hereby incorporated by reference in its entirety.

TECHNICAL FIELD

Provided herein are methods for measuring the size distribution and/or hardness of rock pieces. Also provided is a method for measuring the volume of rock pieces.

BACKGROUND

In a typical mining operation, blasting is a first step of rock size reduction carried out at a mine site or rock quarry in order to remove ores from their natural beds. The blasted material may be subsequently transported by dump trucks and dumped into a crusher to reduce particle size. A typical processing line at a mine after blasting might comprise a primary and secondary crusher, followed by a grinding mill to further reduce particle size before physical separation and/or chemical extraction of one or more minerals.

A significant amount of the energy used in a typical open-pit mine operation is spent in such rock size reduction, often referred to as "comminution". According to various estimates, comminution consumes about 3% of the world's electrical energy. A study on the distribution of energy in the various stages of rock size reduction process shows that blasting accounts for 3-5%, crushing 5-7% and grinding 90% of the total energy used. Indeed, energy efficiency is less than 1% in industrial grinding processes. One of the causes of the low efficiency of the grinding mill is the high variability of the size distribution and hardness of rock pieces fed to the process downstream of crushing.

In the laboratory, a number of techniques are available for measuring rock size distributions, but none are based on a direct measure of the rock volume. That is, the rock volume is extrapolated from other measured values. For example, sieving is based on the measurement of the smallest side area of the rock particle and laser beam diffraction computes the volume from a calibrated curve of volume and laser beam diffraction angle. In addition, most of the commercially available units that are automated, high-speed and contactless for measuring the rock size distribution cannot measure rock samples containing pieces larger than 3 mm. One example, W. S. Tyler CPA technology (https://wstyler.com/particle-analysis-equipment/wstyler-cpa/) of a rare technology allowing an automated measurement of rock pieces larger than 3 mm, is a limited 2D image analysis based technology, which cannot directly measure the volume of the rock pieces. In the laboratory, the measurement of rock particles larger than 1 mm is often performed by wet and/or dry sieving, which is both time consuming and expensive.

In the past number of years, research and development efforts have focussed on 2D image analysis techniques. However, 2D image analysis often involves determining the volume of the rock from its random exposed area, which adds additional dispersion to the measured size distribution. Thus, similar to sieving and laser beam diffraction, the technique does not provide a direct measure of rock volume.

The 2D image analysis technique is subject to further limitations. Digital imaging rock size sensors were installed in crushing plants for measuring ore size distribution of the grinding mill feed stream as it was transported on a conveyor belt. One of the main problems reported was the sampling error caused both by the ore segregation on the belt and the feeding process itself, which transfers the fine material before the coarser blocks on the conveyor belt in order to reduce the wear on the belt. To address this, it has been proposed to install the rock size sensors on the rock excavation shovel or at the crusher truck dumping station, where the sampling error is believed to be reduced significantly. Another reported advantage of taking measurements at these locations is that the measurement is conducted on run-of-mine ore after blasting before any further size reduction in the crusher. However, this necessitates taking the measurements in the outside environment. Since outdoor light conditions cannot be controlled at this stage, some mine operators have been forced to totally abandon the technology.

Other reported limitations of existing 2D rock size photo sensor technologies are (1) a reduced rock fragment delineation accuracy due to the presence of fine particle clusters, multi-colour mineral mixtures, uneven surface textures and poor lighting conditions; (2) an over-estimation of the average rock size by imaging compared to that measured by sieving due to the flat presentation of rock fragments to the camera; (3) a stereological correction error associated with the evaluation of a 3D size distribution from a 2D surface measurement; (4) a restricted visible bandwidth of fragment sizes defined by the camera resolution, scene size and depth of focus; (5) sampling error associated with the large size fragment and heterogeneity of the blast fragmentation; and (6) a bias sampling error due to fragments overlapping and the presence of sand on the surface of the rock.

The industry has attempted to improve the accuracy of the 2D rock size photo sensor technologies in exterior light conditions through the application of 2D classical image analysis algorithms, but to no avail. Despite the development of numerous methods for image filtering and intensity enhancement, optical rock photo size sensor suppliers have concluded that proper lighting intensity and uniformity are essential for the methods to operate efficiently insofar as they are required for automated delineation of rock fragments. However, as noted above, light conditions in an external environment are not ideal and cannot be controlled easily.

A number of three-dimensional (3D) imaging systems have been proposed to overcome some of the limitations of the 2D technology. Adaptation of a 3D imaging technique based on a laser profiler for the measurement of run-of-mine ore has been commercialized and the device was designed to fit over a conveyor belt. A 3D imaging system based on stereo vision has also been reported. The system employs two cameras, which allows 3D information to be gathered. The 3D image information is used to calculate rock fragment sizes, volumes and masses. It was reported that the resulting 3D image is less dependent on the lighting conditions. Despite their recognized improvements over existing 2D technology, 3D imaging systems, however, do not address the measurement of run-of-mine ore size distribution as the rock fragments free fall, such as from the haul truck into a crusher. Thus, the inventors have identified that it would be desirable to develop a method that accurately measures size distribution and hardness of the material as it is fed to a crushing stage, such as when the material free falls as it is being dumped into a crusher. Accurate measurement of these two parameters at this particular stage is the first step in developing process control strategies that will minimize their impact on milling efficiency.

However, challenges identified herein for measuring rock particle size at this particular stage of the process include: (1) the variable speed of the rock as it free falls; (2) the sample representativeness in each size class of the ore size distribution as they are cross related; (3) the long measurement distance of the free fall of the rock (e.g. 17 m); (4) the vibration of equipment and the dusty environment where the measurement is conducted; and (5) the variable weather and lighting conditions inherent to outside environments.

Moreover, a commercially acceptable method of measuring rock hardness on-line is not yet available. A prototype reliant on a model based analysis of the crusher data has provided promising results but such a hardness method requires an evaluation of the rock size reduction ratio achieved by the crusher and therefore is reliant on an accurate size measurement of the free falling rock as it is dumped into the primary crusher (Bilodeau et al. 2008, Couët et al. 2016). Two-dimensional (2D) imaging size sensors have been tested with limited success in measuring the rock size distribution feeding the primary crusher. However, the information provided was often found unreliable and not sufficiently accurate for use in the development of a rock hardness measurement method. Variations in the external light conditions were identified as a limiting factor.

SUMMARY

The embodiments disclosed herein seek to overcome one or more of the above-identified problems and/or to provide a useful alternative to known technology.

An exemplary embodiment includes a method for measuring the size distribution of falling rock pieces comprising: (a) projecting at least one laser line on the falling rock pieces by a laser device; (b) capturing images of the falling rock pieces at an angle from the at least one laser line by at least one camera; and (c) obtaining size distribution data of the falling rock pieces based on data obtained from a topographical map generated from captured images resulting from step (b).

A further exemplary embodiment includes a method for measuring the size distribution of falling rock pieces comprising: (a) projecting a laser line on the falling rock pieces by a laser device; (b) capturing images at an angle from the laser line by at least one camera; (c) executing programmable instructions for a computer processor to carry of the steps of: (i) receiving the captured images from the at least one camera and producing a topographical map of the falling rock pieces from the captured images; (ii) obtaining at least one of the volume and area of individual rock pieces from the topographical map; (iii) conducting a data analysis on at least one of the volume and area measurements of the rock pieces to reduce at least one of sampling and measurement errors; (iv)obtaining size distribution data of the falling rock pieces based on the data analysis of step (iii); and (d) determining a hardness index for rock pieces from the size distribution data determined in step (iv).

Another exemplary embodiment includes a computer implemented method for measuring the size distribution of falling rock pieces comprising: (i) receiving captured images of the falling rock pieces from at least one camera and producing a topographical map of the falling rock pieces from the captured images; (ii) obtaining at least one of the volume and area of individual rock pieces from the topographical map; (iii) conducting a data analysis on at least one of the volume and area measurements of the rock pieces to reduce at least one of sampling and measurement errors; and (iv) determining size distribution data of the falling rock pieces based on the data analysis of step (iii); and (v) determining a hardness index for rock pieces from at least the size distribution data determined in step (iv).

A further exemplary embodiment includes a computer implemented method for measuring a volume of falling rock pieces, the method comprising executing programmable instructions for the computer to carry out the steps of: (a) determining a minimum rock weight of the falling rock pieces from a sampling model to eliminate or reduce sampling error; (b) capturing images of the falling rock pieces fed in a stream between at least two laser scanners, wherein the falling rock pieces are fed in a layer so that at least a substantial volume of the falling rock pieces can be visualized and measured; (c) producing two topographical maps of the falling rock pieces from the captured images from step (b); and (d) obtaining the volume of individual rock pieces from the topographical map by adding half-volumes measured from each of the two topographical maps.

Another exemplary embodiment includes a computer implemented method for measuring a volume of falling rock pieces, the method comprising executing programmable instructions for the computer to carry out the steps of: (a) determining a minimum rock weight of the falling rock pieces from a sampling model to eliminate or reduce sampling error; (b) capturing images of the falling rock pieces fed in a stream between at least two laser scanners, wherein the falling rock pieces are fed in a layer so that at least a substantial volume of the falling rock pieces can be visualized and measured; (c) producing two topographical maps of the falling rock pieces from the captured images from step (b); (d) obtaining the volume of individual rock pieces from the topographical map by adding half-volumes measured from each of the two topographical maps; and (e) evaluating the rock size distribution from the measured volume of the rock pieces.

A further exemplary embodiment provides a computer implemented method for correcting measurement and/or sampling error in a topographical map obtained from images captured by a camera of falling rock pieces, the method comprising executing programmable instructions for the computer to carry out the steps of: (a) correcting the size of the falling rock pieces obtained from data in the topographical map by reducing or eliminating error due to rock overlap, rock sample heterogeneity, or a combination thereof, thereby producing a corrected topographical map; (b) measuring, in the corrected topographic map resulting from step (a), a smallest area of a side of the rock pieces; (c) estimating a rock free-falling speed variance from a light intensity map of the falling rock pieces and correcting rock surface and volume; (d) filtering rock size measurements obtained in step (c) using a model, thereby producing model adjusted data; (e) producing an output of particle size distribution of the rock pieces in computer readable format based on the model adjusted data from step (d) of filtering; and (f) determining a hardness index for rock pieces from at least the size distribution data determined in step (e).

A further exemplary embodiment provides an apparatus comprising a non-transitory computer-readable storage medium storing a computer-executable program for implementing a method for measuring size distribution of falling rock pieces, the method comprising: (a) projecting a laser line on the falling rock pieces by a laser device in communication with said apparatus; (b) capturing images at an angle from the laser line by at least one camera in communication with said apparatus; (c) generating a topographical map from captured images resulting from step (b); and (d) obtaining size distribution data of the falling rock pieces based on data obtained from the topographical map.

A further exemplary embodiment provides an apparatus comprising a non-transitory computer-readable storage medium storing a computer-executable program for implementing a method for measuring the volume of falling rock pieces, the method comprising executing programmable instructions for a computer to carry out the steps of (a) determining a minimum rock weight of the falling rock pieces from a sampling model to eliminate or reduce sampling error; (b) capturing images of the falling rock pieces fed in a stream between at least two laser scanners, wherein the falling rock pieces are fed in a layer so that at least a substantial volume of the falling rock pieces can be visualized and measured; (c) producing two topographical maps of the falling rock pieces from the captured images from step (b); and (d) obtaining the volume of individual rock pieces from the topographical map by adding half-volumes measured from each of the two topographical maps.

DETAILED DESCRIPTION

Provided herein is a method for measuring the size distribution of falling rock pieces, such as when rock pieces are transferred from a transport vehicle to a stage of further comminution, as described below. The method comprises: projecting a laser line on the falling rock pieces by a laser device; capturing images at an angle from the laser line by at least one camera; and obtaining size distribution data of the falling rock pieces based on data obtained from a topographical map generated from the captured images. This method generally provides a volume-based rock size distribution determination. A volume-based size distribution measurement method may permit characterization of the form of the rock pieces based on the entire 3D measurement information.

The size distribution of the falling rock pieces is measured at mine sites, rock quarries and in other applications in which the size of rock pieces is determined. The rock pieces are typically at least 1 mm, or at least 1 cm in diameter. An example of a suitable range of rock sizes is 0.001 m to 3 m in diameter, or 0.001 m to 1.5 m in diameter, or 0.01 m to 1.5 m in diameter. Rock size data can be used in blasting operations to improve size distribution of material fed to crushers and/or grinders. The rock size data can also be used for evaluating a run-of-mine rock hardness index (Bilodeau et al. 2008) from the crusher operating data through a more accurate evaluation of the reduction ratio achieved at a crusher, such as a primary crusher.

As mentioned, at a mining site, blasting removes ores from their natural beds. The blasted material may be subsequently transported by vehicles or by other transport means and dumped into a crusher that reduces the particle size of the rock pieces. One or more crushers may be employed so that the material can be processed into finer particles in a subsequent grinding stage.

Figure 1:
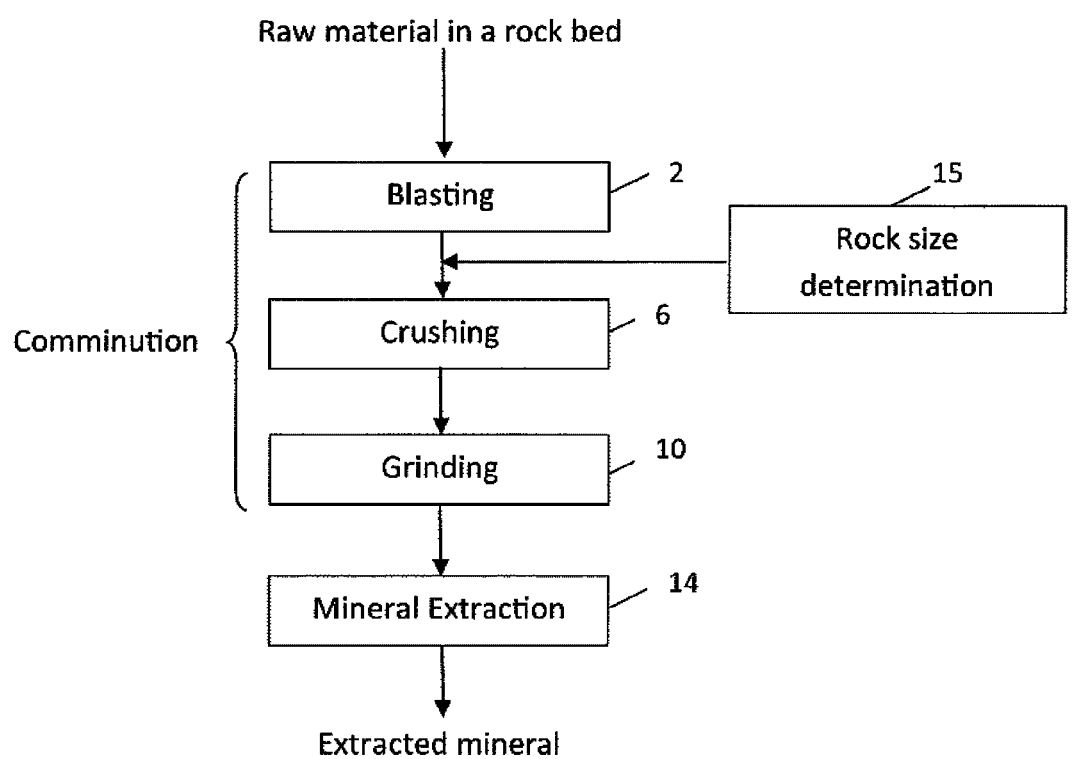
FIG. 1 is a simplified flow diagram for comminuting rock obtained from a rock bed and extracting mineral therefrom according to one embodiment described herein.

FIG. 1 outlines a simplified flow diagram for processing rock and extracting mineral therefrom that incorporates methods and systems according to certain embodiments disclosed herein. Raw material in a rock bed is first subjected to blasting 2 using known techniques. The blasted material is transported by trucks to a crushing step 6 in which the blasted material is subjected to further size reduction by crushers. Rock size determination 15 is carried out on the blasted material as it is introduced to a crusher in the crushing stage 6. The crushed rock is then subjected to grinding 10 to further reduce the rock to a predetermined final particle size. The material resulting from grinding 10 may then be fed to a mineral extraction stage 14 in which mineral is removed from the ground material using chemical extraction or other techniques.

Figure 2:
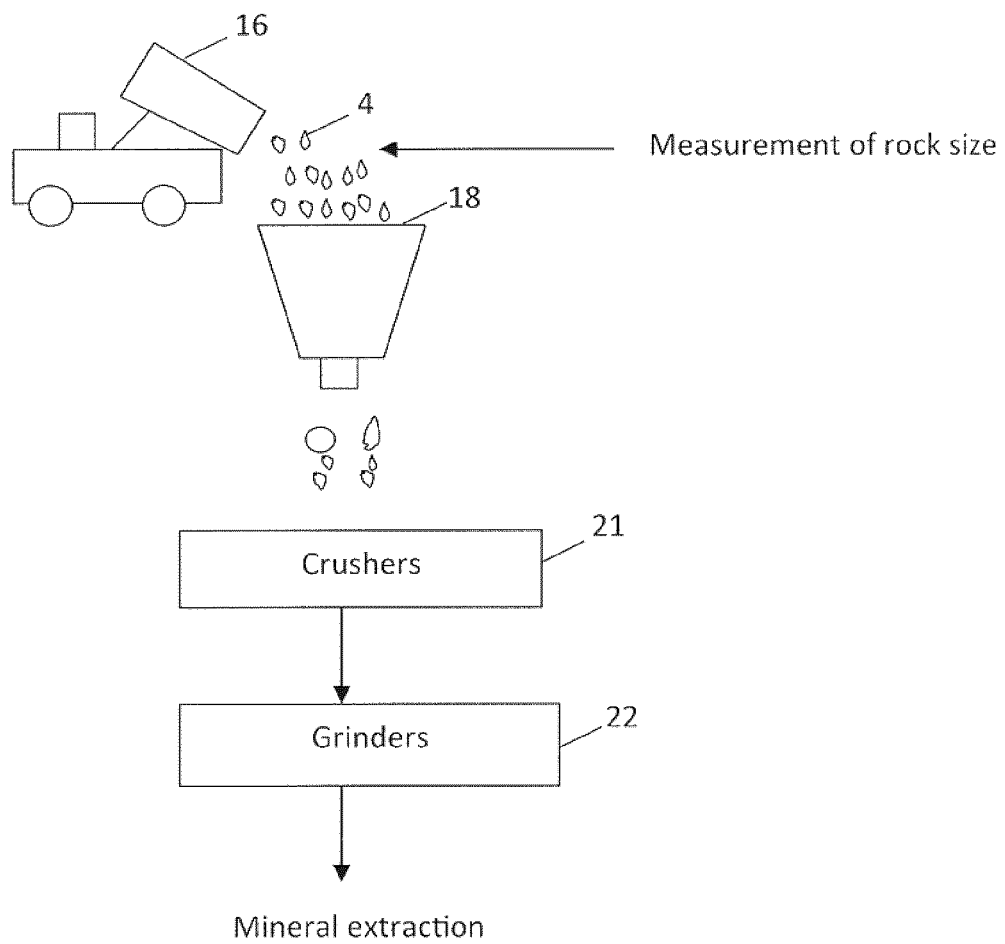
FIG. 2 is a flow diagram showing in more detail the stage at which measurement of falling rock pieces is conducted in accordance with an embodiment described herein.

As shown in the example depicted in FIG. 2, the sizes of the falling rock pieces of blasted material 4 are measured as they are in free fall, such as from a dump truck 16 as the material is fed to a rock crusher 21 or a series of crushers. At a mine, typically more than one crushing stage may be employed, in which case the blasted rock particles 4 are fed to a primary rock crusher, which is omitted from FIG. 2 for simplicity. The crushed rock particles are subsequently fed to grinding mill 22 for further comminution. The ground material may then be sent to mineral extraction as described in FIG. 1.

The size distribution measurement may be conducted in a range of environmental conditions, including full darkness, in the presence or absence of precipitation and/or under dusty conditions.

Measurement of the size distribution of falling rock pieces is carried out by 3D laser scanner technology, which includes a laser source that projects a laser line within the flow of the falling rock pieces and at least one camera, which captures images at an angle determined by those of skill in the art with respect to the laser line projected across the falling rock pieces. The angle of the camera and the distance between the camera and the laser source are selected to allow an adequate visualisation of the surrounding laser line all along the rock pieces being measured; they are selected as a function of the measurement distance, the camera lens, and the required depth measurement range.

Figure 3:
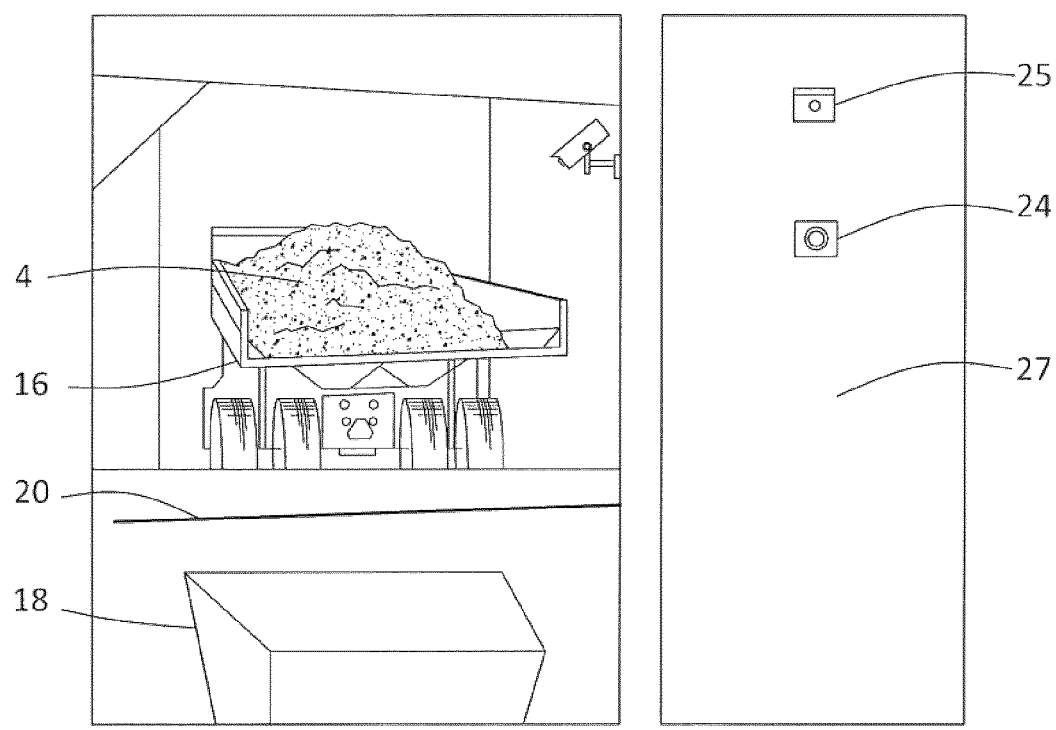
FIG. 3 is a drawing showing a laser line and camera for capturing images of the falling rock pieces in accordance with an embodiment described herein.

A typical arrangement is shown in FIG. 3 which depicts a non-limiting embodiment showing the dump truck 16 before it dumps the blasted rock pieces 4 into a hopper 18 positioned below ground level (where "ground level" is considered here to be where dump truck 16 is located). In this particular example, a laser source unit 24, which is installed on a facing wall 27, projects a laser line 20 behind the dump truck 16. In the embodiment shown in FIG. 3, the laser line is shown projected around 30 cm below the ground level, and a camera 25 is located about 2 m above the laser source unit 24 positioned at an angle from the projected laser line 20. These values are illustrative only and can be adjusted as required.

Figure 4:
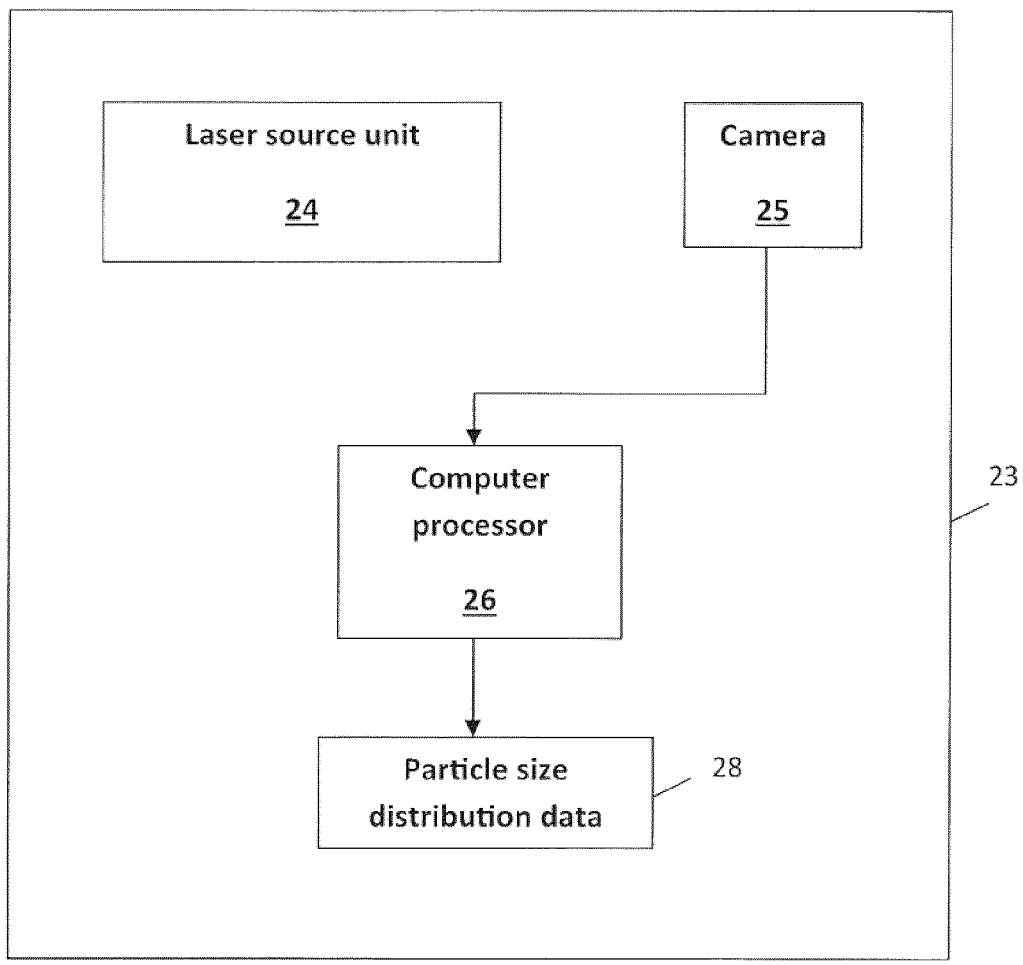
FIG. 4 shows various functionalities of a system for determining rock particle size distribution in accordance with certain embodiments.

FIG. 4 is a block diagram showing a system 23 for measuring particle size distribution of falling rock pieces, such as from the dump truck 16. The laser source unit 24 projects the laser line 20 across the line of travel of rock pieces falling from the dump truck 16. The camera 25 captures a series of images of the falling rock measured at an angle from the laser line 20. The images from the camera 25 are input to a computer processor 26, which in turn outputs particle size distribution data 28 of the falling pieces. The particle size distribution data 28 can be displayed as a histogram and/or in a cumulated percent passing size curve.

Figure 5A:
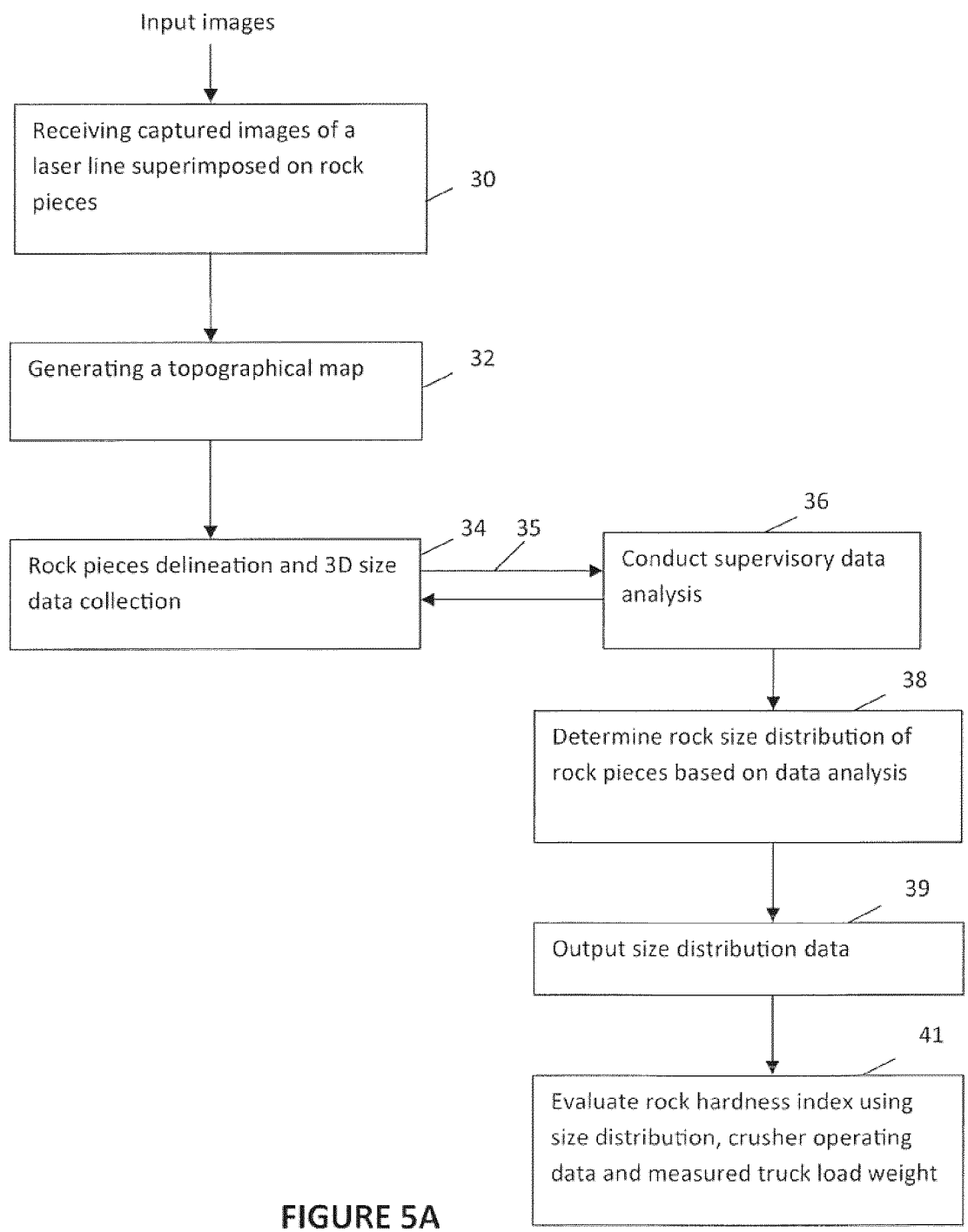
FIG. 5A is a diagram depicting the functionalities of a computer processor for determining rock size distribution based on input from the camera in accordance with certain embodiments.

FIG. 5A shows a processing method providing more detail of the functionalities carried out by computer processor 26. Images of the laser line superimposed on rock particles from camera 25 are received in step 30 by the computer processor 26. A topographical map is generated at step 32 in FIG. 5A after receiving captured images of the laser line superimposed on the rock pieces in step 30. A supervisory data analysis step 36 iteratively controls the execution of a number of subsequent image analyses in step 34 for identifying individual rock pieces and measures their corresponding three dimensional size data in step 34. Image analysis parameters in step 34 are optimized at each of the iterations 35 for a pre-determined rock size class being identified in order to minimize or reduce the negative impact of sampling and measurement errors. Based on the supervisory data analysis 36, the size distribution of the rock pieces is determined in step 38 and outputs size distribution data in step 39. The computer processor 26 can output the size distribution data in output step 39, for example as a histogram, although the data can be output in other formats as well.

The size distribution output at step 39 may be used for determining a hardness index in 41 for rock 4 in a dump truck 16 using the size distribution data output at step 39. As would be appreciated by those of skill in the art, this is determined from a corresponding reduction ratio measured at a crusher (e.g., a primary crusher), the energy consumption of the crusher and the weight of the rock 4 in dump truck 16.

Figure 6A:
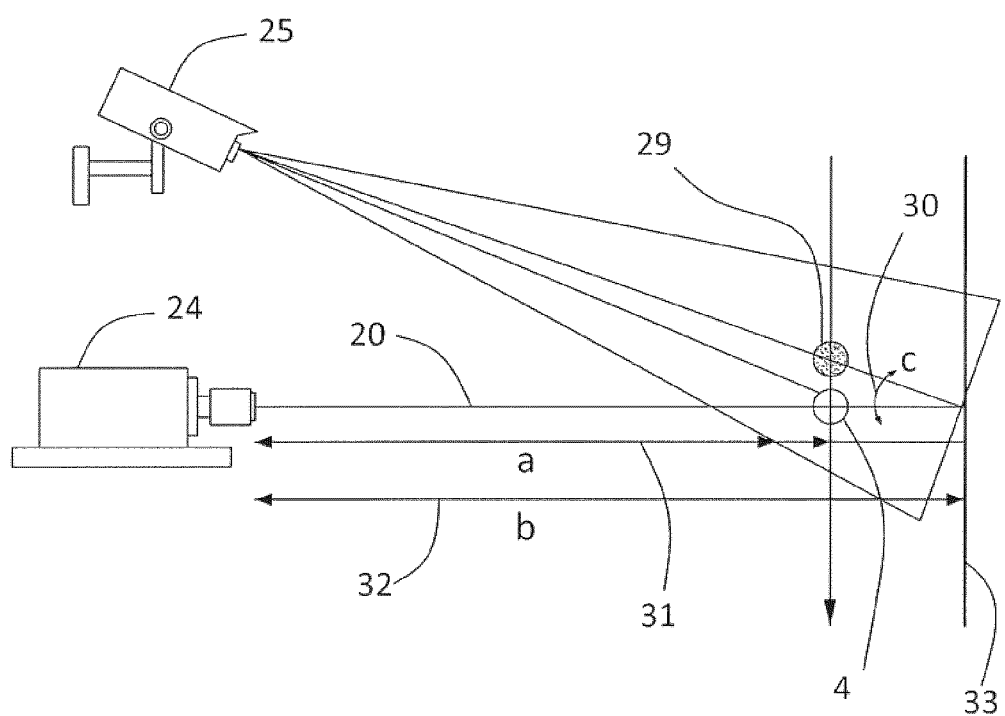
FIG. 6A is a diagram depicting the functionalities of a computer processor evaluating the rock speed variance from the light intensity map produced by the laser scanner.

Turning now to FIG. 6A, there is shown a drawing that depicts in more detail how the topographical map is generated in step 32 of FIG. 5A from the captured images of falling rock. Generating the topographical map in step 32 includes taking images of the laser line 20 superimposed on the rock flow 47. An example of a suitable frequency of image capture of the laser line 20 superimposed on the falling rock pieces by the camera 25 is in the range of 1000 frames/second, but other frequencies can be utilized as desired. The consecutive, captured images of the superimposed laser line (e.g., 1000/second) define the 3D form of the rock pieces as they pass in front of the laser line 20. The horizontal and depth size data of rock pieces are computed using the position of the line on the image taken by the camera 25, the distance between the camera 25 and the laser source unit 24 and the angle of the camera 25. Basic geometrical rules known to those of skill in the art are applied in the calculation. The estimated free fall rock speed and the image capture frequency (e.g., 1000 frames/second) then define the distance between two consecutive lines, which is used for computing the rock size data in the vertical direction. The collected horizontal, vertical and depth size data of the rock flow defines the topographical map of the rock flow in 32. A light intensity map of the rock flow, which is similar to a 2D image captured by a line scan camera, is captured from the laser light reflected from the rock pieces. The light intensity map is used by the supervisory data analysis step 36 for evaluating the rock falling speed and correcting the size measurement accordingly in the vertical direction.

Figure 5B:
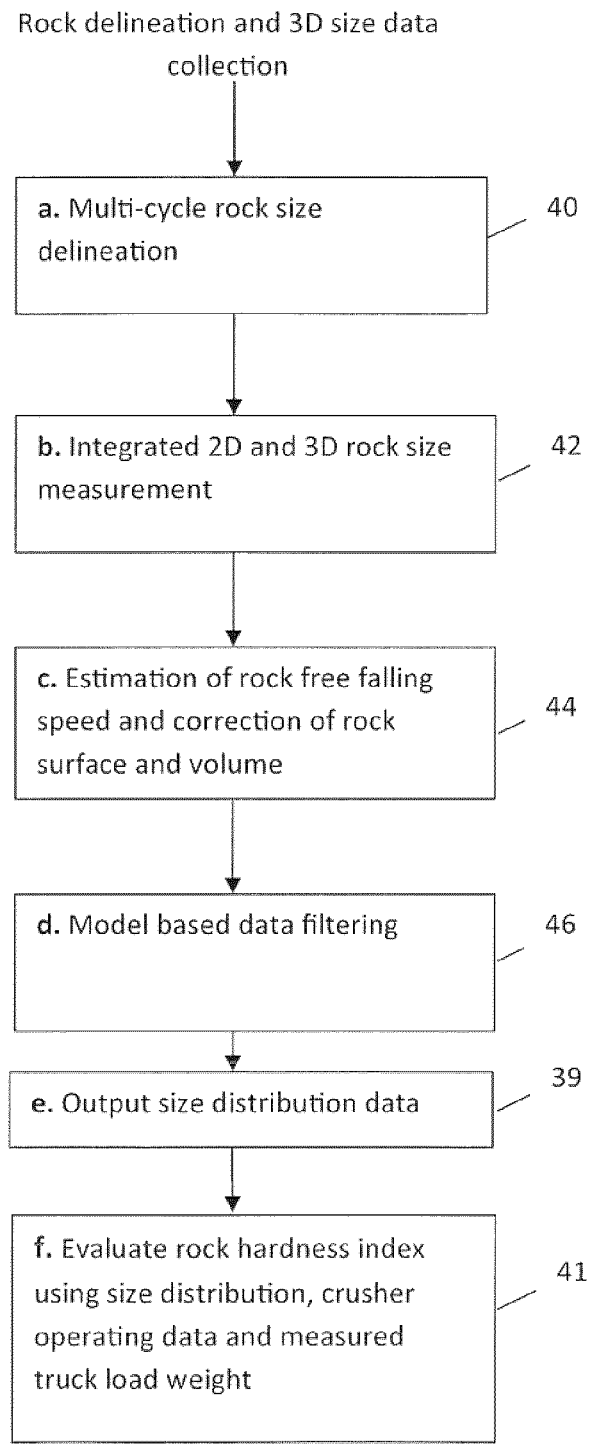
FIG. 5B is a diagram depicting the functionalities of a computer processor supervising the analysis of 3D size data information in order to a model based data adjusted rock size distribution.
Figure 6B:
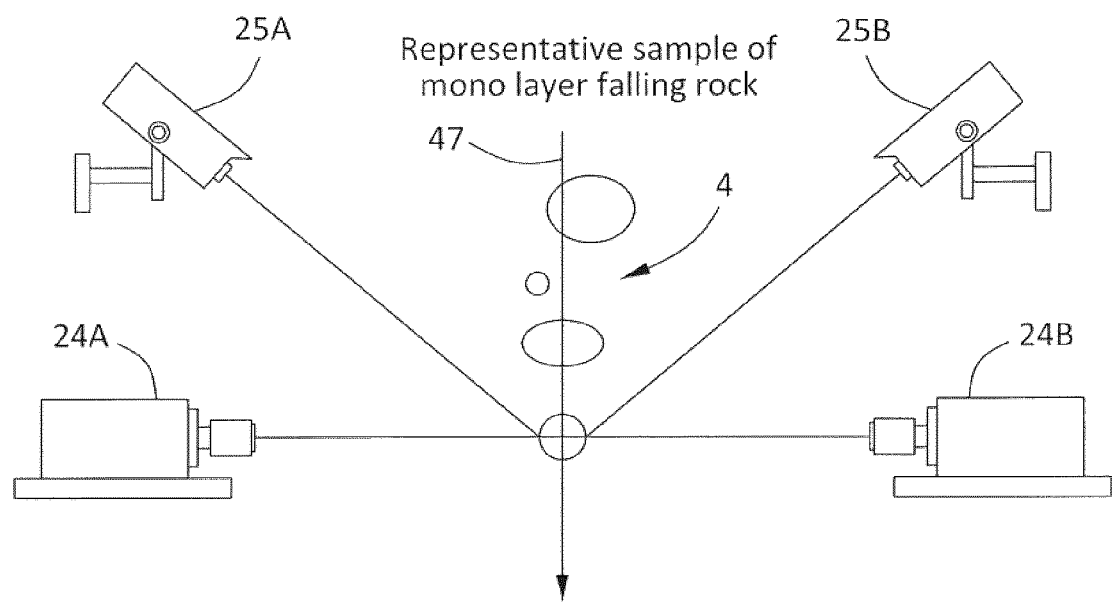
FIG. 6B is a drawing showing two laser lines and a camera system for capturing images of the falling rock pieces in accordance with the laboratory device that measures the full volume of rock pieces.

FIG. 5B shows more detail of the steps carried out by the supervisory data analysis step 36 shown in FIG. 5A. The supervisory data analysis 36 can be used to apply know-how in rock sizing to minimize the impact of sampling and measurement errors and determines the rock size distribution accordingly. In this example, the supervisory data analysis includes the following steps:

a. A multi-cycle rock size delineation step 40 (FIG. 5B) iteratively delineates rock pieces and measures corresponding 3D size data. Rock delineation parameters are optimized at each of the iterations for the size classes being analyzed and/or the form and position of rock pieces being researched and identified. The rock pieces identified at each of the iterations are then grouped in a single data set and rock pieces identified as duplicates are removed. Step 40 minimizes the sampling error caused by rock overlap and/or adapts the rock delineation algorithms to account for the heterogeneity of the rock samples being measured.

b. An integrated 2D and 3D rock size measurement step 42 identifies and measures in the topographic map the smallest of three side areas of each rock piece that have been delineated by the multi-cycle rock size delineation step 40. Step 42 measures the smallest side area of each delineated rock piece, which usually corresponds to the particle size measured by sieving. Such a measurement method, through use of the 3D rock size information, reduces the higher measurement dispersion usually observed in a 2D rock size analysis measurement, which is caused by the heterogeneous form of the particle and its random presentation to the camera 25. This also makes the measured size distribution more consistent with a size distribution measured by sieving, which is an established laboratory method for measuring size distribution. It is also an alternative to volume size measurement, which can be biased in the industrial application of the rock size determination method disclosed herein because only one side and only the first layer of the rock flow is visible to the camera 25. As a result, the volume of the rock pieces is not entirely seen by the camera and in addition the deeper fine size layers are not visible to the camera 25 and may be underestimated, while the coarser size fraction may be over-estimated. Volume size measurement is not biased in a laboratory scale application when a single layer of rock pieces is measured from both sides and the depth information collected by two cameras, such as is cameras 25A 25B, shown in FIG. 6B, on each side. The cameras are matched and processed accordingly in 36 for ensuring the complementarity of the information collected by camera 25A and 25B. A size distribution is computed from a volume size measurement.

c. The rock free-falling speed variance is extracted in step 44 from the light intensity map, which is produced in association with the topographic map. Two, non-limiting, examples are provided herein as strategies for measuring speed variance. In accordance with one embodiment, as illustrated in FIG. 6A, a shadow 29 of a given rock piece 4 appears occasionally on the intensity map when isolated rock particles cross the laser light reflected from the background wall 33 to the camera 25. The vertical distance between the shadow 29 and the rock piece 4 is evaluated from known geometric rules based on a known angle 30 of the camera 25 and the distances 31 and 32 (shown as "a" and "b" in FIG. 6A), respectively, separating the laser source 24 from the rock piece 4 and the background wall 33. The time for covering this distance, which corresponds to a number of pixel lines in the light intensity map is then estimated from the camera speed frequency. Speed is then evaluated by dividing the distance by the time. A rock image pattern recognition step may also be included for full automation. The method can be used initially off-line after identifying visually a number of rock pieces and their shadow on the light intensity map. A size correction factor discussed below will be measured at the beginning, mid-way and at the end of the rock flow for estimating the rock speed variance. The size correction factor will be applied to the particle size measurements as needed.

In accordance with another embodiment, the strategy for evaluating the free fall rock speed variance is based on frequency analysis of the light intensity image. According to this strategy a 2D fast Fourier Transform is performed to decompose the light intensity image into its sine and cosine components. The output of the transformation represents the image in the frequency domain. A relative average power spectrum, which defines the average relative contribution of each frequency in this image, is then computed in both the horizontal and the vertical direction.

Figure 6C:
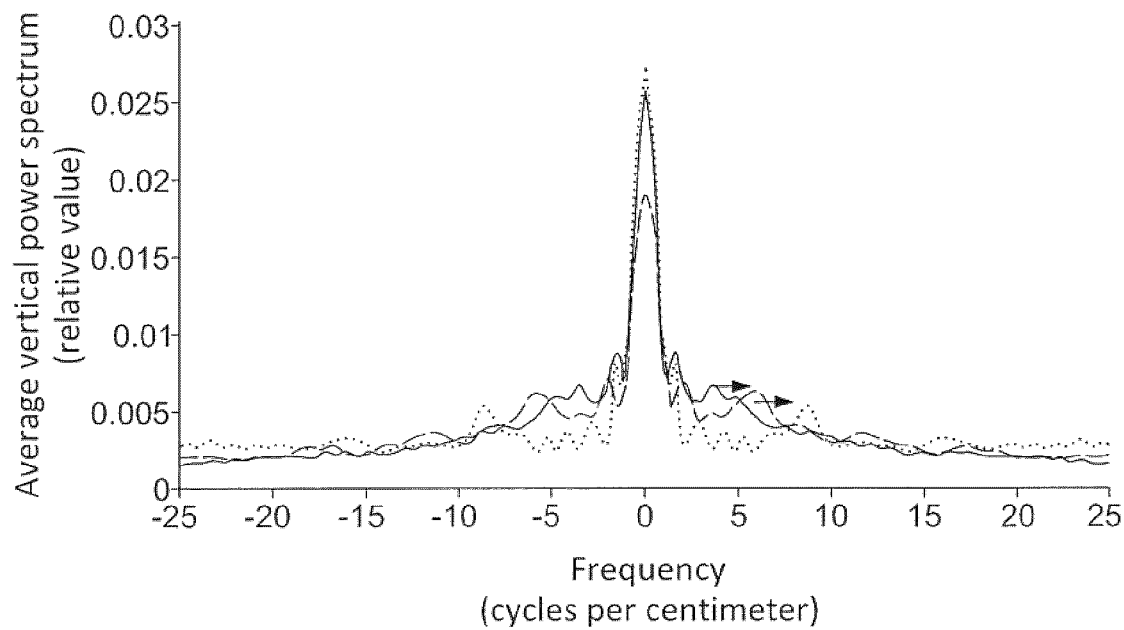
FIG. 6C is a graph showing the average power spectrum measured in the vertical direction in accordance with its correlation with the free fall rock speed variation and the method proposed for evaluating the rock speed variance of a monolithic rock size distribution.

This method for evaluating rock speed variance has been demonstrated using a monolithic rock size distribution at a laboratory scale. The results verified that the rock size measurement variation resulting from the free fall speed variation of the rock could be evaluated from the average power spectrum measured in the vertical direction (FIG. 6C). Two consecutive 10% speed increases in the vertical direction corresponds to two consecutive shifts of about 2 cycles/centimeter for the most significant frequency range on the average power spectrum measured in the vertical direction. These are identified by the two arrows in FIG. 6C.

Figure 6D:
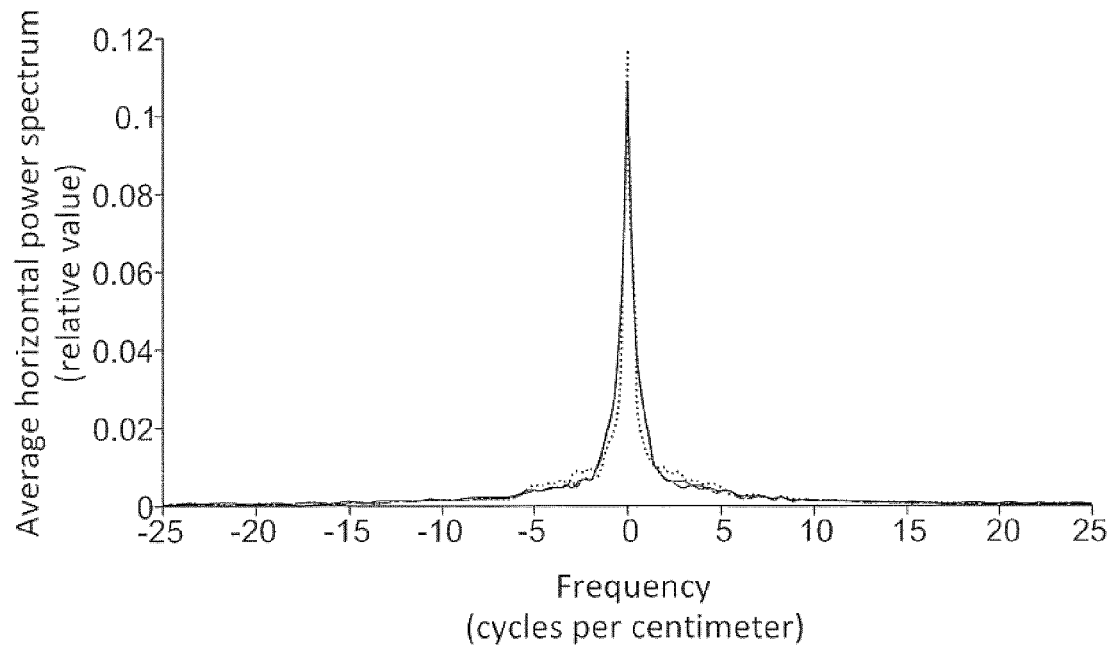
FIG. 6D is a graph showing the average power spectrum measured in the horizontal direction in accordance with its independency toward free fall rock speed variation and the method proposed for evaluating the rock speed variance of a monolithic rock size distribution.

The two consecutive 10% shifts in the free fall rock speed were introduced in the image by dropping three balls of similar sizes from three different heights as explained above. The average power spectrum in the horizontal direction (FIG. 6D) for the same image was constant and therefore independent of the free fall speed variation.

Figure 6E:
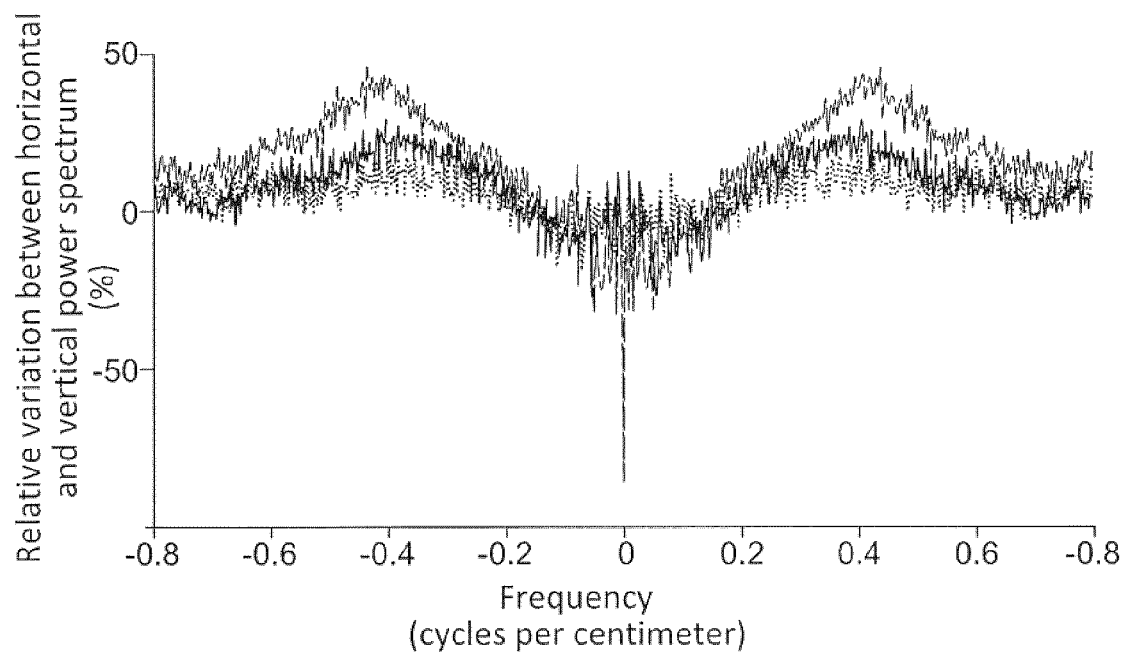
FIG. 6E is a graph showing difference between horizontal and vertical average power spectrum that are correlated with rock fall speed variation in accordance with the resulting size of the rock and the method proposed for evaluating the rock speed variance of a natural and more complex size distribution, as measured in a rock quarry.

In the case of natural, and consequently more complex size distribution, as measured in a rock quarry, such a rock size variation was not perceptible on the average power spectrum analysed in the vertical direction. However, the presence of a more populous size class among the rock pieces may make this size change perceptible around the size corresponding frequency range. It has been demonstrated, qualitatively, for a number of rock images captured at the rock quarry, that the difference between the horizontal and vertical average power spectrum is proportional to the rock fall speed of the truck discharge and, therefore, to the resulting size of the rock (FIG. 6E). Such an observation is consistent with the fact that only the vertical average power spectrum is dependent on the rock speed variation.

In accordance with this embodiment, the rock free-falling speed variance measurement comprises a calibration method for correlating measurements with rock size. Examples of calibration parameters may include, but are not limited to, the average rock speed, the average size and the form of the rock.

d. A model based data filtering step 46 addresses the sampling and measurement error in rock size measurement. A Rosin Rammler model is calibrated on quality rated raw data and a new set of adjusted data is calculated from the calibrated model. The size distribution calculated from the model adjusted data is more accurate in both the coarse and fine size range of the distribution.

e. After the model based data filtering step 46, size distribution data of the falling rock is output.

f. The size distribution output at step 39 may be used for determining a hardness index in 41 for rock 4 in dump truck 16 or other transport vehicle. The determination factors include the measured size distribution and a corresponding reduction ratio at the primary crusher, the measured energy consumption of the primary crusher and the measured weight of the vehicle load.

Also provided herein is a method for measuring the volume of falling rock pieces. Such a method can be used in a laboratory setting to measure rock volume. The method (FIG. 6B) includes capturing images of falling rock pieces 4 by using at least two laser source units 24A and 24B facing one another. The rock pieces 4 fall between two facing cameras 25A and 25B. In order to provide a representative sample to the rock volume size measurement system, the minimum required sample weight may first be evaluated using a P.Gy sampling model pre-calibrated on the rock material. A vibrating feeder (not shown) may be used to introduce the rock pieces 4 as a monolayer 47 in order to make the volume of all or a significant portion of the rock pieces 4 visible to the cameras 25A and 25B, thereby minimizing the sampling and measurement errors. Two topographical maps of the falling rock pieces 4 are generated from the captured images from the two cameras 25A and 25B. The topographical maps are generated as described previously with reference to FIG. 6A. The volume of the individual rock pieces 4 are then obtained from the topographical maps by adding half-volumes obtained from each of the two topographical maps. In accordance with one embodiment, the volume calculation method includes an image synchronisation algorithm that matches the information collected by each camera, an automated horizontal and depth calibration method, and a volume measurement algorithm that adjusts the half-volume measured by each camera as a function of a strategic and imaginary central plane, which is defined on-line for each test based on the cameras depth reading intercept; such a correction ensures full complementarity and avoids duplication in volume measurement.

Light interference between the two laser scanners is minimized through selection of light intensity frequency and a corresponding light frequency filter for each of the two cameras 24A and 24B.

In some embodiments, one or more steps of the methods described herein can be implemented by one or more general purpose computers, or other programmable device, programmed in accordance with the principals discussed herein. In various embodiments, a general computer processor programmed in accordance with various principles described herein is provided in the cloud of a cloud computing environment. In some embodiments, a general computer processor programmed in accordance with various principles is provided at one or more servers or nodes.

Digital computer systems or devices programmed to perform particular functions pursuant to instructions from program code that implements features of the methods described herein may be special-purpose computers particular to the methods described herein. Computer program code implementing one or more methods described herein may be distributed to users on a non-transient, computer readable storage medium such as, for example, a floppy disk, CD-ROM, or flash memory data storage device, or other suitable distribution storage medium, and may be copied to a hard disk, RAM, or other suitable intermediate, non-transient computer readable storage medium, on a computer. When the programs are to be run, they will be loaded either from their distribution medium or their intermediate storage medium into the execution memory of the computer, configuring the computer to act in accordance with the method of this invention.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that certain of the described program components and systems can generally be integrated together in a single software product being executed in one or more networks or packaged into multiple software products for execution in the one or more networks.

One or more steps of the processes or methods described in this specification can be performed by one or more programmable processors executing one or more computer programs to perform functions by operating on input data and generating output.

Various embodiments can be implemented in a cloud computing system that includes, and/or is in communication with, a back end component, e.g., as a data server, or that includes a middleware component, e.g., an application server, or that includes a front end component, e.g., a computer having a GUI or a Web browser through which an operator can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

EXAMPLES

Example 1

Prototype for Measuring Particle Size Distribution of Falling Rocks

A prototype of a 3D laser scanner measured particle size distribution of free falling rock particles at a mine site. The prototype (see e.g., FIG. 3) included a laser source, a camera and a data acquisition card. Data acquisition and 3D image analysis software collected raw data into a computer, computed the topographical map of the rock pieces, delineated the rock pieces, measured their volume and/or area and presented the results in a histogram.

The prototype was developed and evaluated at pilot scale and during a 2-day period in a lime rock quarry under winter conditions (−20° C. and snow). The objective was to evaluate the potential of the technology for measuring the ratio of particles less than 1 cm, which has proven to be difficult to measure accurately with the existing 2D technology and which reduces significantly the efficiency of the lime production process.

The 3D scanner was installed in the crusher area housing, which has one side thereof opened for truck circulation and dumping. The camera was facing the truck dumping location and was therefore exposed to outdoor light variations (FIG. 3). The system, including the laser device, cameras and computers, was also exposed to outdoor temperature variations since the crusher housing was not heated. Dust was more abundant than expected because it did not disperse significantly due to the confines of the enclosure.

The available working distance was reduced to about 10 m in the crusher area structure and the 3D scanner prototype was designed accordingly.

The 3D rock size sensor was tested in the presence of sun, darkness, dust, vibration, and at temperature below −20° C. for two days from 8 h00 to 15 h00. Rock discharge was filmed in parallel with high speed 2D video cameras, which were equipped with a 16 mm lens. The 2D camera is a Basler acA2040-25gc GigE camera with the CMOSIS CMV4000 CMOS sensor, which delivers 25 frames per second at 4 MP resolutions (http://www.baslerweb.com). MATLAB based software was built for extracting 2D images from the video at a variable time rate. Known rock size analysis software was used for analysing the 2D images.

A number of laboratory experiments were subsequently designed for better understanding the developed prototype. This included comparative studies with known 2D technologies. The 2D technologies that were compared with the 3D technology of the present embodiments are a high-speed video camera, a line scan camera and a pseudo line scan camera using a laser light source. Similar software and hardware configurations were used for minimizing any non-related differences among the different technologies.

Exemplary operating conditions of the 3D laser scanner prototype are provided in Table 1 below:

TABLE 1

Operating conditions specified for the 3D laser scanner prototype

| Operating Conditions | Range of values |
|---|---|
| Rock block size (m) | 0.01 to 1.5 |
| Maximal working distance (m) | 16.5 to 17.5 |
| Environmental conditions | Snow, rain, sun, full darkness, dust |
| Laser line position above ground floor (m) | 0.3 to 1 |
| Rock average falling speed (m/s) | 2 |

Figure 7:
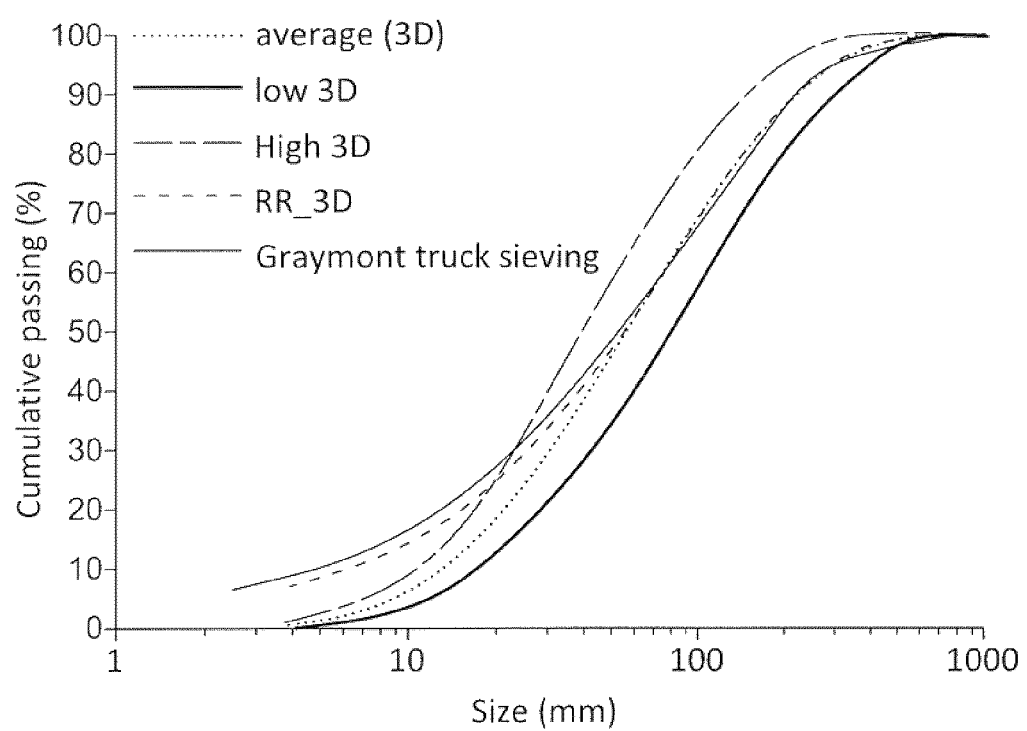
FIG. 7 is a graph showing cumulative passing (%) of rock particles versus size of rock particles as measured by methods known in the art and 3D methods according to embodiments.

FIG. 7 shows the average size distribution measured over the 2-day period with the low and high limit calculated from the measured standard deviation. The measured size distribution was compared to a calibrated Rosin Ramler size distribution curve and a size distribution measured by sieving a few years earlier on similar run-of-mine rock. The size distribution measured by sieving was consistent with the size distribution measured with the 3D scanner between 50 and 1000 mm. Such agreement confirms the representativeness of the larger size fraction in the distribution and also demonstrates an adequate calibration of the 3D scanner parameters. A discrepancy was, however, observed between the two curves in the fine size range. The gap began around 50 mm and appeared to reach a maximum value around 10 mm, which has already been identified as the low size limit detection of the 3D scanner within the pilot scale test work. The calibration of a Rosin Ramler model on the 3D scanner raw data resulted in a size distribution curve that was consistent over the full size range with the size distribution measured by sieving. Thus, the calibration of a Rosin Ramler model was required for evaluating the percentage of fine particles (<1 cm), which was evaluated at about 15%.

Example 2

Prototype for Measuring Volume of Falling Rock Pieces

In this example a prototype for measuring the volume of falling rock pieces in laboratory was tested. The prototype (see e.g., FIG. 6B) included capturing images of falling rock pieces by using at least two cameras and two laser source units facing one another. The rock pieces fell between two facing cameras and laser sources. Two topographical maps of the falling rock pieces were generated from the captured images from the two cameras. The topographical maps were generated as described previously with reference to FIG. 6A. The volumes of the individual rock pieces were then obtained from the topographical maps by adding half-volumes obtained from each of the two topographical maps. The volume calculation method included an image synchronisation algorithm that matched the information collected by each camera, automated horizontal and depth calibration method, and a volume measurement algorithm that adjusted the half-volume measured by each camera as a function of a strategic and imaginary central plane, which was defined on-line for each test based on cameras depth reading intercept. Such a correction ensured full complementarity and avoided duplication in volume measurement. Light interference between the two laser scanners was minimized through selection of light intensity frequency and a corresponding light frequency filter for each of the two cameras.

Figure 8:
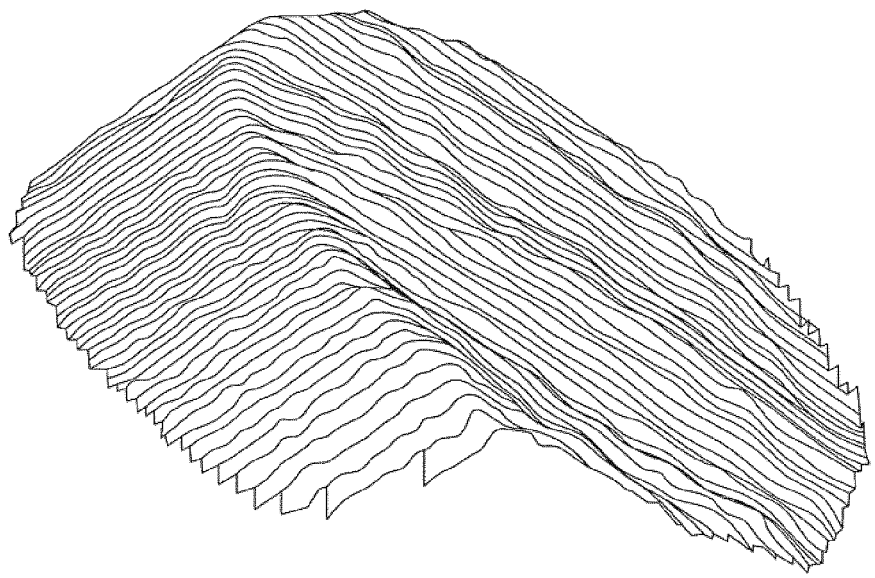
FIG. 8 is the 3D representation of each portion of a rock disc (1.8 cm thick by 5 cm diameter) as captured and by each of the two cameras and measured by the laboratory scale version of the 3D scanner.
Figure 8:
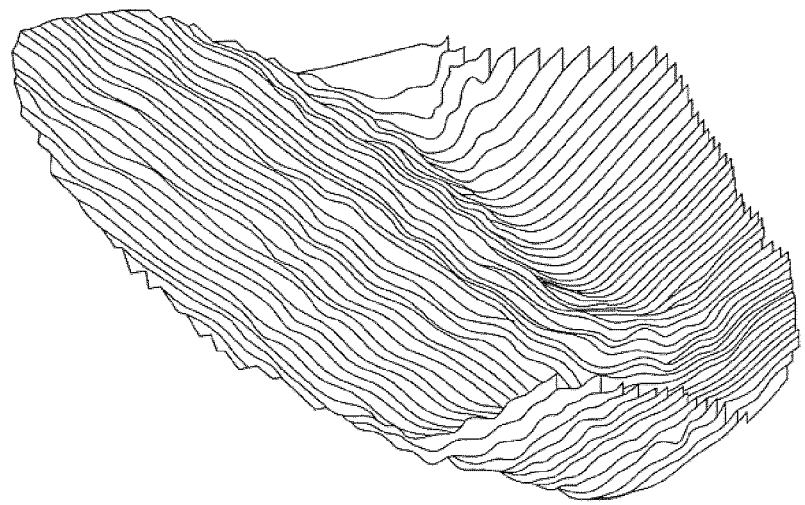

The prototype was evaluated in laboratory on numerous objects of various forms and sizes. The objective was to evaluate the capability of the technology for measuring objects of different forms and sizes and to get an estimate of the measurement accuracy before optimisation. The volume of the objects was measured in parallel with standard volume measurement methods for comparison purposes. FIG. 8 shows the 3D representation of each portion of one of the measured objects as captured by each of the two cameras; the object was a rock disc of 1.8 cm thick by 5 cm diameter. The measurement accuracy of the method was evaluated between 5% to 15% depending of the form and diameter size of the object, which varied between 5 and 65 mm.

The foregoing embodiments are illustrative only and should not be construed to limit the scope of the invention as defined by the claims.

REFERENCES

BILODEAU, M., LABRIE, D., BOISCLAIR, M., BEAUDOIN, R., ROY, D. and CARON, G., 2008. Impact of electronic blasting detonators on downstream operations of a quarry. Minerals and Metallurgical Processing, 25(1), pp. 32-40.

COUËT, F., MAKNI, S., GAGNON, G., ROCHEFORT, C., 2016, Applying online ore hardness estimation to SAG operation and optimisation, IMPC 2016 : XXVIII International Mineral Processing Congress Proceedings.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method for measuring the size distribution of falling rock pieces comprising:
    (a) projecting at least one laser line on the falling rock pieces by a laser device;
    (b) capturing images of the falling rock pieces at an angle from the at least one laser line by at least one camera; and
    (c) obtaining size distribution data of the falling rock pieces based on data obtained from a topographical map generated from captured images resulting from step (b).

2. The method of claim 1, wherein step (c) comprises:
    producing a topographical map of the falling rock pieces from the images captured in step (b);
    (ii) obtaining at least one of the volume and area of individual rock pieces from the topographical map;

(iii) conducting a data analysis on at least one of the volume and area measurements of the rock pieces to reduce at least one of sampling and measurement errors; and (iv) obtaining size distribution data of the falling rock pieces based on the data analysis in step (iii).

3. The method of claim 1, wherein the rock pieces are at least 1 cm in diameter.

4. The method of claim 1, wherein the falling rock pieces are from a blasting operation.

5. The method of claim 1, wherein the method measures the falling rock pieces in free fall as the rock pieces are transferred from a rock transporter to a rock crusher.

6. The method of claim 5, wherein the rock transporter is a haul truck and the rock crusher is a primary rock crusher.

7. The method of claim 1, wherein two cameras capture images of the laser line.

8. The method of claim 1, wherein the method comprises projecting two side-by-side laser lines on the falling rock pieces by two laser devices.

9. The method of claim 1, wherein volume and area measurements are obtained from the topographical map and the data analysis is conducted on the volume and/or area of the rock pieces.

10. The method of claim 1, wherein the falling rock pieces are from a load of rocks in a vehicle and wherein the method additionally comprises measuring a rock hardness index of the load of rocks in the vehicle, which measurement is obtained from the obtained rock size distribution, operating data of a crusher and a measured weight of rock pieces in the load of the vehicle.

11. The method of claim 1, wherein the method is a computer-implemented method.

12. The method of claim 1, wherein the method additionally comprises correcting measurement and/or sampling error in the topographical map generated from the captured images.

13. The method of claim 12, wherein correcting measurement and/or sampling error comprises the steps of:

(1) correcting the size of the falling rock pieces obtained from data in the topographical map by reducing or eliminating error due to rock overlap, rock sample heterogeneity, or a combination thereof, thereby producing a corrected topographical map;

(2) measuring, in the corrected topographical map, a smallest area of a side of the rock pieces;

(3) estimating a rock free-falling speed variance from a light intensity map of the falling rock pieces and correcting rock surface and volume;

(4) filtering rock size measurements from the corrected rock surface and volume using a model, thereby producing model adjusted data;

(5) producing an output of corrected size distribution of the rock pieces based on the model adjusted data.

14. The method of claim 13, wherein the step of correcting the size of the falling rock pieces comprises measuring the size of coarse and fine rock fragments from the falling rock pieces separately.

15. The method of claim 13, wherein the step of measuring a smallest area of a side of the rock pieces comprises measuring the smallest side area of rock pieces that have been corrected.

16. A computer implemented method for correcting measurement and/or sampling error in a topographical map obtained from images captured by a camera of falling rock pieces, the method comprising executing programmable instructions for the computer to carry out the steps of:

(a) correcting the size of the falling rock pieces obtained from data in the topographical map by reducing or eliminating error due to rock overlap, rock sample heterogeneity, or a combination thereof, thereby producing a corrected topographical map;

(b) measuring, in the corrected topographic map resulting from step (a), a smallest area of a side of the rock pieces;

(c) estimating a rock free-falling speed variance from a light intensity map of the falling rock pieces and correcting rock surface and volume;

(d) filtering rock size measurements obtained in step (c) using a model, thereby producing model adjusted data;

(e) producing an output of particle size distribution of the rock pieces in computer readable format based on the model adjusted data from step (d) of filtering; and (f) determining a hardness index for rock pieces from at least the size distribution data determined in step (e).

17. A computer implemented method for measuring the volume of falling rock pieces, the method comprising executing programmable instructions for a computer to carry out the steps of:

(a) determining a minimum rock weight of the falling rock pieces from a sampling model to eliminate or reduce sampling error;

(b) capturing images of the falling rock pieces fed in a stream between at least two laser scanners, wherein the falling rock pieces are fed in a layer so that at least a substantial volume of the falling rock pieces can be visualized and measured;

(c) producing two topographical maps of the falling rock pieces from the captured images from step (b); and (d) obtaining the volume of individual rock pieces from the topographical map by adding half-volumes measured from each of the two topographical maps.

18. An apparatus comprising a non-transitory computer-readable storage medium storing a computer-executable program for implementing a method for measuring size distribution of falling rock pieces, the method comprising:

(a) projecting a laser line on the falling rock pieces by a laser device in communication with said apparatus;

(b) capturing images at an angle from the laser line by at least one camera in communication with said apparatus;

(c) generating a topographical map from captured images resulting from step (b); and (d) obtaining size distribution data of the falling rock pieces based on data obtained from the topographical map.

19. The apparatus of claim 18, wherein step (c) of the method comprises:

i) producing a topographical map of the falling rock pieces from the images captured in step (b);

(ii) obtaining at least one of the volume and area of individual rock pieces from the topographical map;

(iii) conducting a data analysis on at least one of the volume and area measurements of the rock pieces to reduce at least one of sampling and measurement errors; and (iv) obtaining size distribution data of the falling rock pieces based on the data analysis in step (iii).

20. The apparatus of claim 18, wherein the rock pieces are at least 3 mm in diameter.

21. The apparatus of claim 18, wherein the falling rock pieces are from a blasting operation.

22. The apparatus of claim 18, wherein the method measures the falling rock pieces in free fall as the rock pieces are transferred from a rock transporter to a rock crusher.

23. The apparatus of claim 22, wherein the rock transporter is a haul truck and the rock crusher is a primary rock crusher.

24. The apparatus of claim 18, wherein two cameras capture images of the laser line.

25. The apparatus of claim 18, wherein the method comprises projecting two side-by-side laser lines on the falling rock pieces by two laser devices.

26. The apparatus of claim 18, wherein volume and area measurements are obtained from the topographical map and the data analysis is conducted on the volume and/or area of the rock pieces.

27. The apparatus of claim 18, wherein the falling rock pieces are from a load of rocks in a vehicle and wherein the method additionally comprises measuring a rock hardness index of the load of rocks in the vehicle, which measurement is obtained from the obtained rock size distribution, operating data of a crusher and a measured weight of rock pieces in the load of the vehicle.

28. The apparatus of any one of claims 18 to 27, wherein the method additionally comprises correcting measurement and/or sampling error in the topographical map generated from the captured images.

29. An apparatus comprising a non-transitory computer-readable storage medium storing a computer-executable program for implementing a method for measuring the volume of falling rock pieces, the method comprising executing programmable instructions for a computer to carry out the steps of:
(a) determining a minimum rock weight of the falling rock pieces from a sampling model to eliminate or reduce sampling error;
(b) capturing images of the falling rock pieces fed in a stream between at least two laser scanners, wherein the falling rock pieces are fed in a layer so that at least a substantial volume of the falling rock pieces can be visualized and measured;
(c) producing two topographical maps of the falling rock pieces from the captured images from step (b); and
(d) obtaining the volume of individual rock pieces from the topographical map by adding half-volumes measured from each of the two topographical maps.

* * * * *

UNITED STATES PATENT AND TRADEMARK OFFICE
CERTIFICATE OF CORRECTION

| | | |
|---|---|---|
| PATENT NO. | : 11,204,241 B2 | Page 1 of 1 |
| APPLICATION NO. | : 16/486065 | |
| DATED | : December 21, 2021 | |
| INVENTOR(S) | : Magella Bilodeau et al. | |

It is certified that error appears in the above-identified patent and that said Letters Patent is hereby corrected as shown below:

In the Claims

Claim 2, Column 14, Line 64, please insert --(i)-- before "producing a topographical map of the falling rock pieces".

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*